United States Patent [19]

Lin

[11] Patent Number: 5,545,167
[45] Date of Patent: Aug. 13, 1996

[54] RETAINING MECHANISM OF VERTEBRAL FIXATION ROD

[76] Inventor: Chih-I Lin, 14292 Spring Vista La., Chino Hills, Calif. 91709

[21] Appl. No.: 419,698

[22] Filed: Apr. 11, 1995

[51] Int. Cl.[6] ................................................ A61B 17/70
[52] U.S. Cl. ........................ 606/61; 606/72; 411/349
[58] Field of Search ................................ 606/61, 60, 72, 606/73, 59, 54, 53; 411/353, 349, 350, 548

[56] References Cited

U.S. PATENT DOCUMENTS

| | | | |
|---|---|---|---|
| 4,657,462 | 4/1987 | Hoen | 411/349 X |
| 5,209,752 | 5/1993 | Ashman et al. | 606/61 |
| 5,246,442 | 9/1993 | Ashman et al. | 606/61 |
| 5,257,993 | 11/1993 | Asher et al. | 606/61 |
| 5,261,909 | 11/1993 | Sutterlin et al. | 606/61 |
| 5,282,801 | 2/1994 | Sherman | 606/61 |
| 5,368,427 | 11/1994 | Pfaffinger | 411/553 |

Primary Examiner—Guy V. Tucker
Attorney, Agent, or Firm—Bacon & Thomas

[57] ABSTRACT

A retaining mechanism of a vertebral fixation rod includes a rod body, a retaining bolt, a U-shaped connection element, and a fastening nut. The retaining bolt is provided at one end thereof with a ring for holding the rod body and at another end thereof with a bolt portion having a rectangular head. The U-shaped connection element is provided at one end thereof with a U-shaped fitting portion dimensioned to fit over the bolt portion of the retaining bolt and is further provided at another end thereof with a connecting portion engageable with a vertebra to be fixed or with a vertebral fixation device. The fastening nut is engaged with the rectangular head of the bolt portion of the retaining bolt. The fastening nut is provided therein with a plurality of bevel slide blocks for causing the retaining bolt to slide along the slide blocks when the fastening nut is rotated, and is further provided with one or more stop elements to engage with the rectangular head of the retaining nut.

15 Claims, 7 Drawing Sheets

RETAINING MECHANISM OF VERTEBRAL FIXATION ROD

FIELD OF THE INVENTION

The present invention relates generally to a vertebral fixation rod, and more particularly to a retaining mechanism of the vertebral fixation rod.

BACKGROUND OF THE INVENTION

The conventional retaining mechanism of the vertebral fixation rod is generally composed of screws for fastening the vertebral fixation elements, such as bone screws, bone hooks, etc., with the vertebral fixation rod. The case in point is the U.S. Pat. No. 5,257,993 disclosing an invention in which the set screw 60 is used to fasten the rod 48 to a receiving slot of the vertebral fixation rod, which is formed by the U-shaped end opening 52 of the hook portion 22 and the transverse opening 90 of the end cap 24. A similar invention is disclosed in the U.S. Pat. No. 4,887,596 in which the fixation rod is fastened by means of adjustment screws 22 and 23. Such prior art methods of fastening an object with a fixation rod by means of the adjustment screws as described above are inherently defective in design in that the adjustment screws are vulnerable to becoming loosened by the vertebral movement, and that the effect of fastening the object with the fixation rod is seriously undermined.

SUMMARY OF THE INVENTION

It is therefore the primary objective of the present invention to provide a vertebral fixation rod having a fastening mechanism which can be fastened to the fixation rod quickly.

It is another objective of the present invention to provide a vertebral fixation rod with a retaining mechanism devoid of the adjustment screws of the prior art.

It is still another objective of the present invention to provide a vertebral fixation rod with a retaining mechanism comprising a distance adjusting washer and/or a direction adjusting washer.

In keeping with the principle of the present invention, the foregoing objectives of the present invention are attained by a retaining mechanism of the vertebral fixation rod, which comprises a rod body, a retaining bolt, a U-shaped connection element, and a fastening nut. The retaining bolt is provided at one end thereof with a retaining ring for holding the rod body and is further provided at another end thereof with a bolt portion having at the top end thereof a rectangular head. The U-shaped connection element is provided at one end thereof with a U-shaped fitting portion for holding the bolt portion of the retaining bolt and is further provided at another end thereof with a connecting portion for fastening a fractured vertebra or a vertebral fixation device. The fastening nut is engageable securely with the rectangular head of the bolt portion of the retaining bolt. The fastening nut is provided therein with a plurality of bevel slide blocks and with one or more stop elements. As the fastening nut is turned, the rectangular head of the retaining bolt is caused to move along the bevel slide blocks and stop at a predetermined position by engaging with the stop elements so as to fasten securely the fastening nut with the rectangular head of the retaining bolt.

The rod body of the present invention is similar in construction to any rod body of the prior art. In addition, any fixation element of the vertebral fixing and retrieving system, such as a bone screw, or the extension portion of a bone hook, may be used as the rod body of the present invention.

The retaining bolt of the present invention may be provided with a close retaining ring or an open retaining ring, depending on the surgical requirements.

The U-shaped connection element of the present invention is preferably provided at the U-shaped fitting portion thereof with a slot for enabling the U-shaped connection element to join with the rod body securely. In the meantime, another end of the U-shaped connection element may be similar in construction to any prior art connecting portion, such as a bone screw, or a bone hook, or a U-shaped fitting element, which is engageable with a vertebral fixation device.

The fastening nut of the present invention is preferably provided with a platform located in the sliding direction of the bevel slide blocks of the fastening nut so as to cause the rectangular head of the retaining bolt of the present invention to be retained on the platform at such time when the retaining bolt is located after being caused to slide along the bevel slide blocks. As a result, the connection area between the retaining bolt and the fastening nut is increased effectively. Such a connection area as described above may be further increased by adding additional bevel slide blocks in the fastening nut. However, the bevel slide blocks so added must be able to cooperate with the rectangular head of the retaining bolt.

The fastening nut of the present invention described above is provided at an appropriate position thereof with one or more stop elements for fastening the retaining bolt which is located. The appropriate position referred to above is the position at which the fastening nut is engageable with the retaining bolt. For example, the appropriate position may be a side or bottom of the rectangular head of the retaining bolt. The stop element which is provided at a circular fastening nut may be a fastening piece or a fastening tenon. If the retaining bolt is provided at the bottom of the rectangular head thereof with a retaining recessed slot or retaining projected slot, the stop element is either a retaining projected slot or a retaining recessed slot, which is engageable with the retaining recessed slot or the retaining projected slot of the rectangular head of the retaining bolt.

Figure 9:
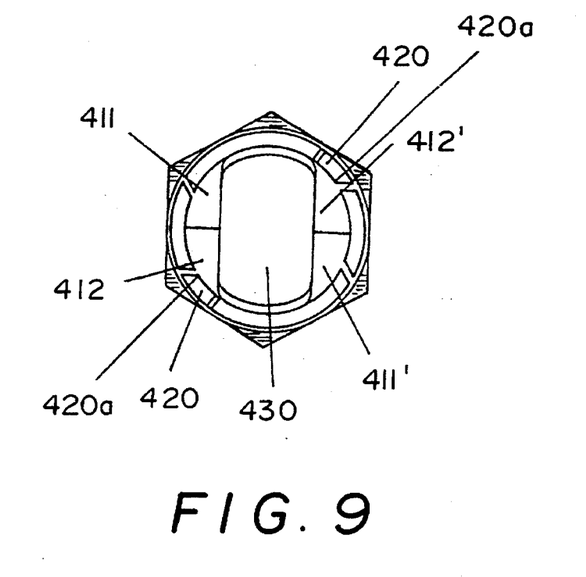
FIG. 9 shows a sectional view of the rod body of the present invention.

The bevel slide blocks of the fastening nut are arranged on two opposite sides of the inner surface of the circular fastening nut such that the interior of the fastening nut is provided with a rectangular space dimensioned to allow the rectangular head of the retaining bolt to pass therethrough. It is suggested that the fastening nut of the present invention is preferably provided with two bevel slide blocks in such a manner that each of these two bevel slide blocks has a bevel slide surface and a platform, and the line connecting the two edges between the platforms and the bevel slide surfaces intersects the central axis of the circular nut of the fastening nut (FIG. 9).

The rectangular space of the fastening nut and the rectangular head of the retaining bolt of the present invention have no specific shape and size; nevertheless they must be able to cooperate with each other. Suppose that R denotes the inner diameter of the fastening nut; 2R, the diameter of the fastening nut; L, the distance between the inner sides of the two bevel slide blocks of the rectangular space of the fastening nut; $I_1$, the length of the long side of the rectangular head of the retaining bolt; and $I_2$, the length of the short side of the rectangular head of the retaining bolt. It is then expected that the diameter (2R) of the fastening nut is greater than the length of the long side of the rectangular head of the retaining bolt, $I_1$, and that the magnitude of the distance between the inner sides of the two bevel slide blocks, L, is between the length of the long side of the rectangular head of the retaining bolt, 11, and the length of the short side of the rectangular head of the retaining bolt, $I_2$.

In order to reinforce the fastening effect of the vertebral fixation rod of the present invention, it is suggested that a washer may be disposed between the U-shaped connection element and the fastening nut. If necessary, an angle-adjusting washer such as the washer 25 disclosed in the U.S. Pat. No. 5,261,909 or a distance-adjusting connection element such as the offset connector 40 disclosed also in the above-mentioned U.S. Patent may be used in conjunction with the present invention.

The foregoing objectives, features and advantages of the present invention will be more readily understood upon a thoughtful deliberation of the following detailed description of the preferred embodiments of the present invention in conjunction with the accompanying drawings.

DETAILED DESCRIPTION OF THE EMBODIMENTS

Figure 1:
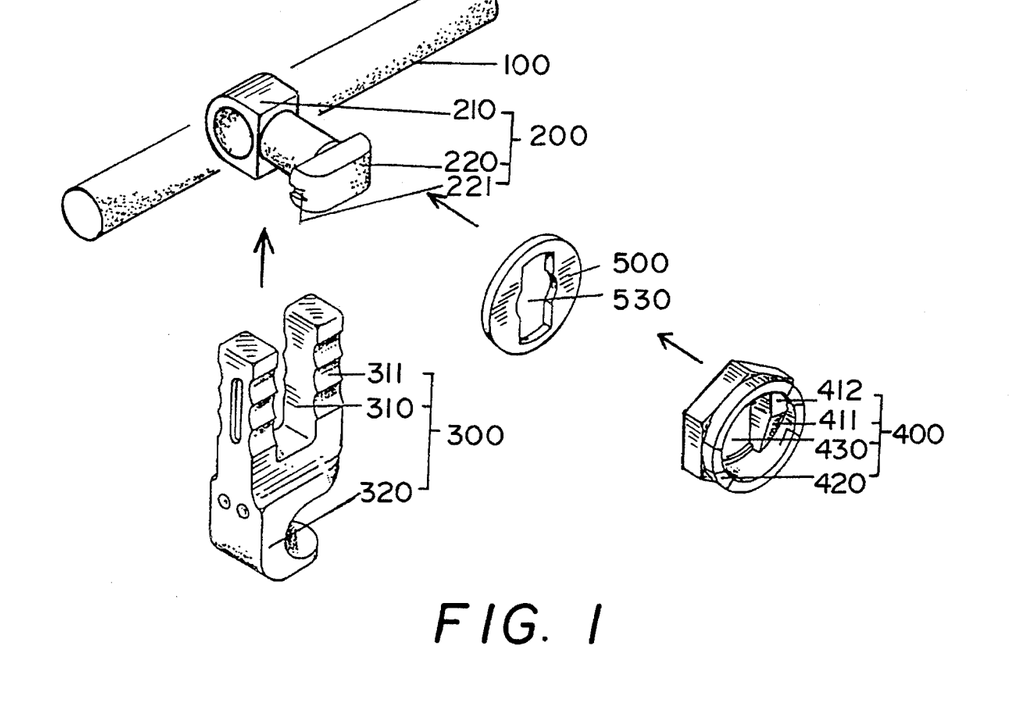
FIG. 1 shows a schematic view of the fastening process of a first preferred embodiment of the present invention.

As shown in FIG. 1, the present invention comprises a rod body 100 which is in fact a vertebral fixation rod, a close retaining bolt 200 having a retaining ring 210 and a bolt portion containing a rectangular head 220 which is provided with a retaining slot 221, a U-shaped connection element 300 having a U-shaped fitting portion 310 and a bone hook (connecting portion) 320, a fastening nut 400 provided with two bevel slide blocks, each of which has a bevel slide surface 411 and a platform 412, and a stop element 420. The present invention further comprises a washer 500 having a fitting hole 530. The fitting portion 310 is provided with a plurality of height adjusting knurls 311 for adjusting the height of the U-shaped connection element in the retaining mechanism of the vertebral fixation rod. The fastening nut 400 has a fitting hole 430 for receiving therein the rectangular head 220 of the retaining bolt 200, which is rotated for a 90-degree angle before being located.

Figure 2:
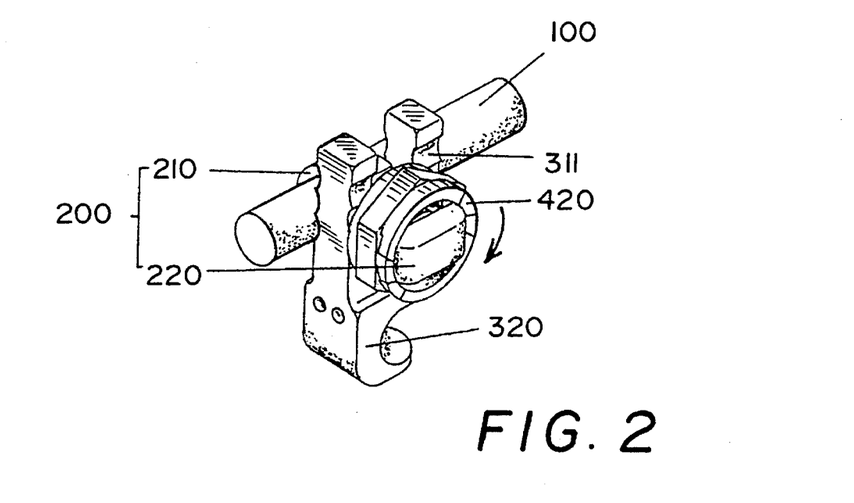
FIG. 2 shows a perspective view of the first preferred embodiment in combination according to the present invention.

FIG. 2 shows the retaining mechanism of the vertebral fixation rod in combination according to the present invention. The reference numerals of FIG. 2 are similar in definition to those of FIG. 1.

A sectional view of the fastening nut 400 is shown in FIG. 9 in which the reference numerals of 411, 412, 420, 430 are similar in definition to the like reference numerals of FIG. 1. The bevel slide surface and the platform of another set are denoted respectively by the reference numerals of 411' and 412'. The stop elements 420 are pushed radially to deform to an extent such that the stop elements 420 are able to elastically contact the sides of the rectangular head 220 when the fastening nut 400 is rotated for near 90-degree, and an inner and front corners 420a of the stop elements 420 are able to engage with the retaining slots 221 of the retaining bolt 200.

Figure 3:
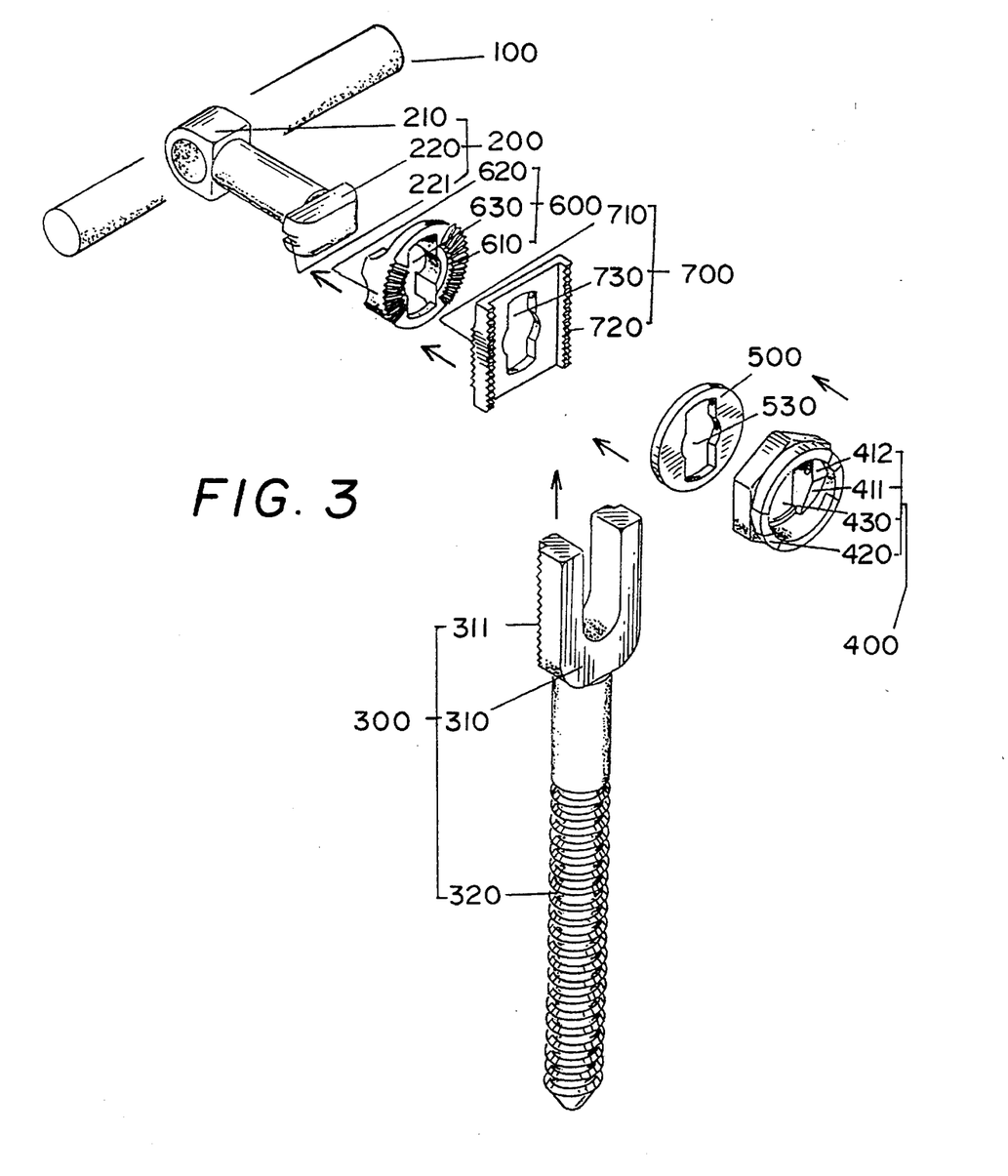
FIG. 3 shows a schematic view of the fastening process of a second preferred embodiment of the present invention.

FIG. 3 shows another retaining mechanism of a vertebral fixation rod according to the present invention which is similar to FIG. 1. The reference numerals of FIG. 3 are similar in definition to those of FIG. 1. The U-shaped connection element 300 has a connecting portion 320 which is a bone screw while the U-shaped fitting portion 310 is provided on one side thereof with fine knurls 311. An angle adjusting washer 600 has angle adjusting knurls 610, an arcuate surface 620 and a fitting hole 630. A height adjusting washer 700 has angle adjusting knurls 710 and a fitting hole 730. In combination, the rod body 100 is fitted into the retaining ring 210 of the retaining bolt 200. The angle adjusting washer is then fitted into the retaining ring 210 and is turned for an angle of about 90 degrees so as to cause the arcuate surface 620 to fit over the rod body 100. Thereafter, the height adjusting washer 700 is fitted thereinto and is turned for an angle of about 90 degrees so as to cause the angle adjusting knurls 710 of the washer 700 and the angle adjusting knurls 610 of the washer 600 to form a specific angle. The U-shaped fitting portion 310 of the U-shaped connection element 300 is fitted such that the angle adjusting knurls 311 and the angle adjusting knurls 720 of the height adjusting washer 700 are knurled. The fastening nut 400 is fastened thereto and is then turned for an angle of about 90 degrees so as to cause the rectangular head 220 of the retaining bolt 200 to slide along the bevel slide surface 411 to the platform 412 where the retaining slot 221 is engaged securely with the stop element 420 of the fastening bolt 400.

Figure 4:
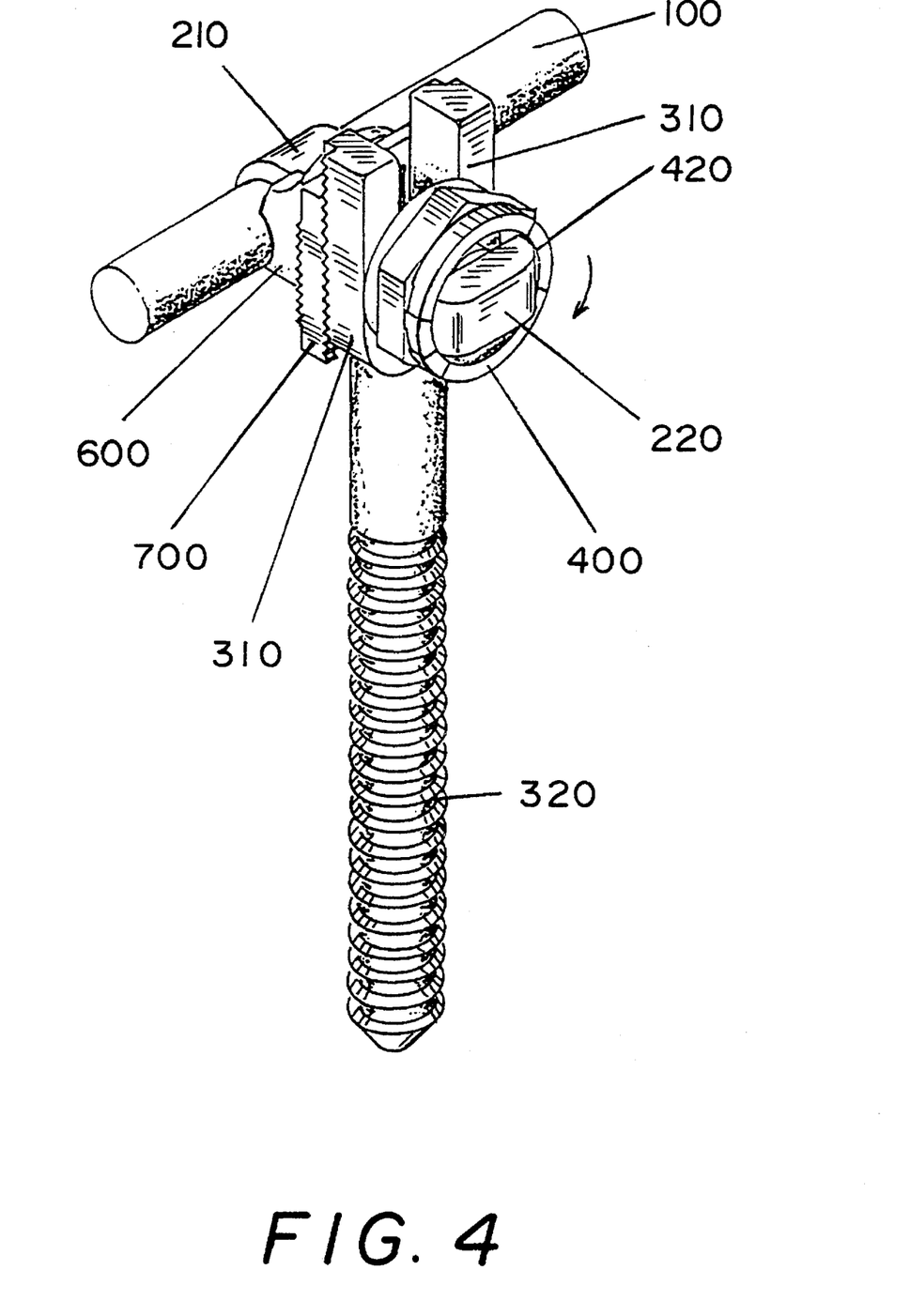
FIG. 4 shows a perspective view of the second preferred embodiment in combination according to the present invention.

FIG. 4 show a perspective view of the retaining mechanism of the vertebral fixation rod in FIG. 3 in combination. The reference numerals of FIG. 4 are similar in definition to those of FIG. 3.

Figure 5:
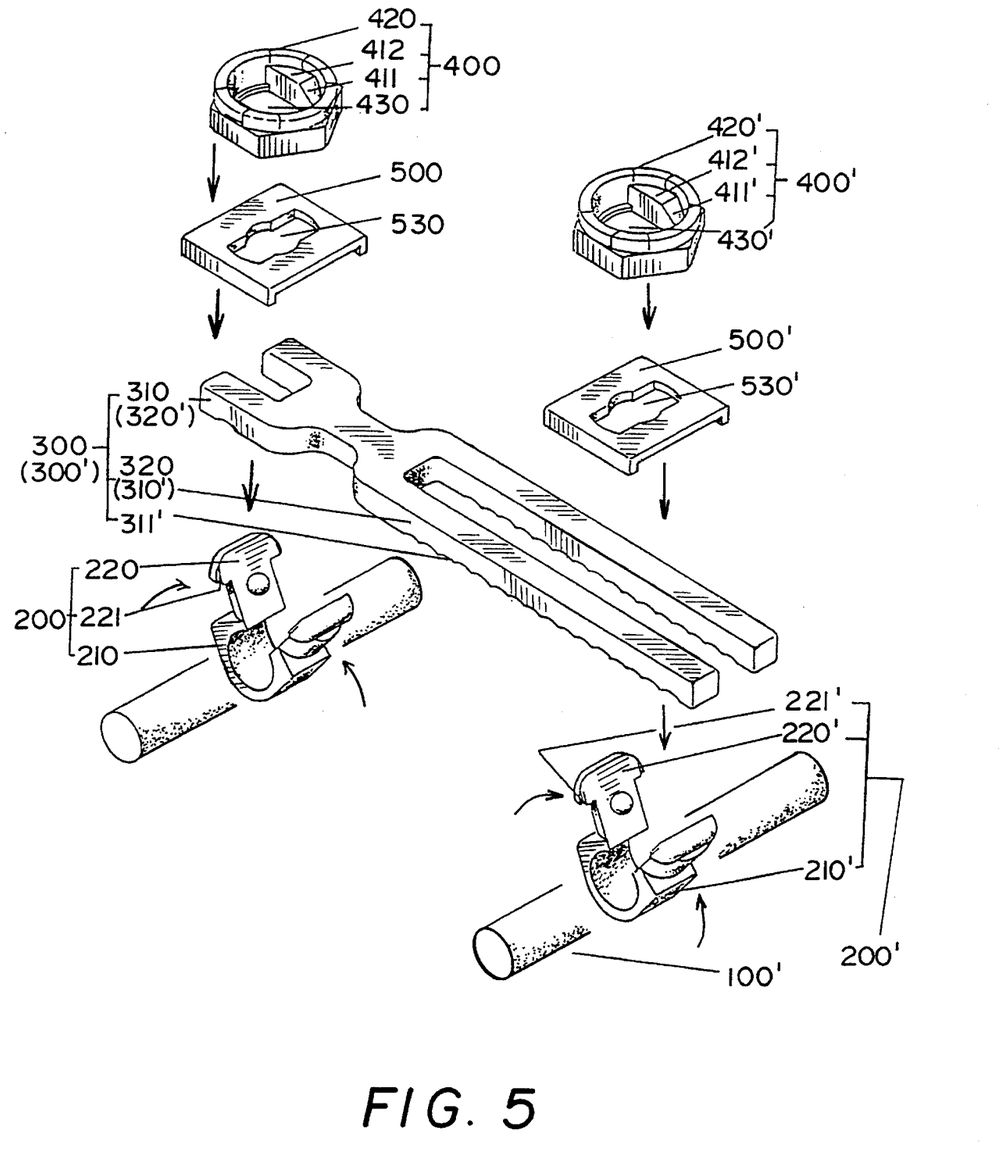
FIG. 5 shows a schematic view of the fastening process of two sets of embodiments in combination according to the present invention.
Figure 6:
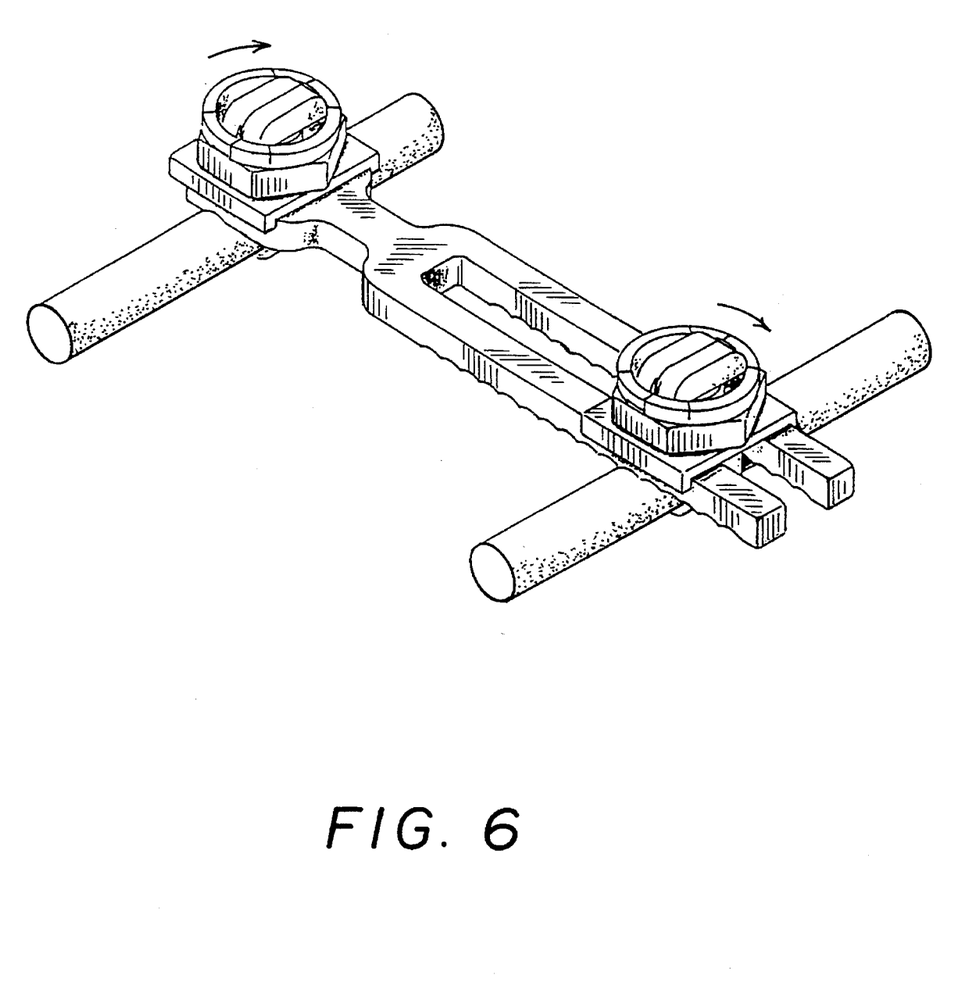
FIG. 6 shows a perspective view of two sets of embodiments in combination according to the present invention.

The combination of two sets of retaining mechanisms of vertebral fixation rods is shown in FIG. 5 in which the reference numerals of 100, 200, 210, 220, 221, 300, 310, 320, 400, 410, 411, 420, 430, 500 and 530 are similar in definition to those of FIG. 1. The reference numerals of another set of the retaining mechanism of the vertebral fixation rod are 100', 200', 210', 221', 300', 310', 320', 400', 410', 411', 420', 430', 500', 530', which are similar in definition to the reference numerals of 100, 200, 210, 220, 221, 300, 310, 320, 400, 410, 411, 420, 430, 500 and 530. The U-shaped connection element 300 and the U-shaped connection element 300' are the same component member. However, the U-shaped fitting portion 310 of the U-shaped connection element 300 is the connecting portion 320' of the U-shaped connection element 300'. Similarly, the connecting portion 320 of the U-shaped connection element 300 is the U-shaped fitting portion 310' of the U-shaped connection element 300'. The retaining bolts 200 and 200' are of an open type. The fastening process is similar in sequence to that shown in FIG. 1. FIG. 6 shows two sets of retaining mechanisms of vertebral fixation rods in FIG. 5 in combination. The reference numerals of FIG. 6 are similar in definition to the like numerals of FIG. 5.

Figure 7:
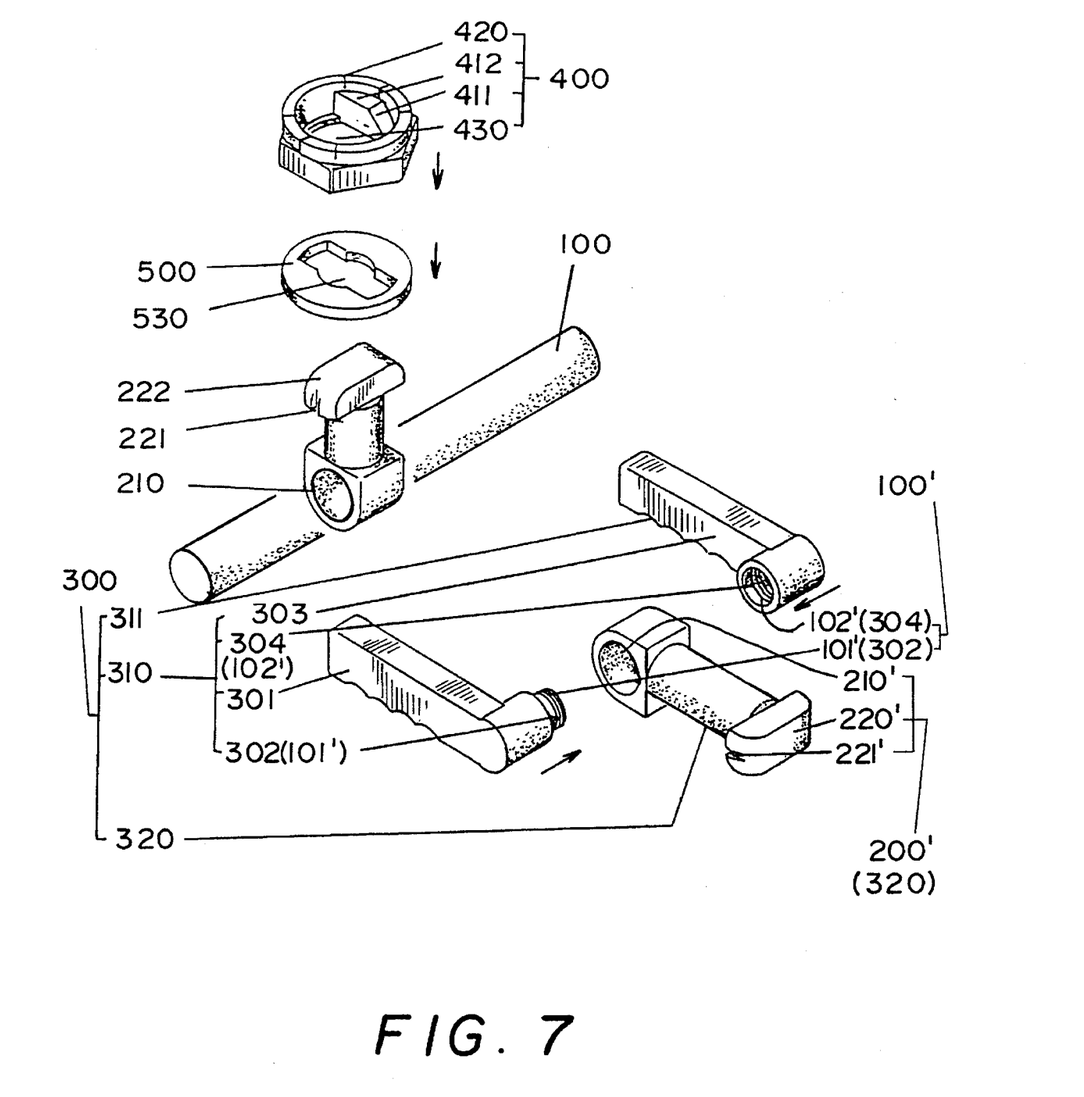
FIG. 7 shows a schematic view of the fastening process of another two sets of embodiments in combination according to the present invention.
Figure 8:
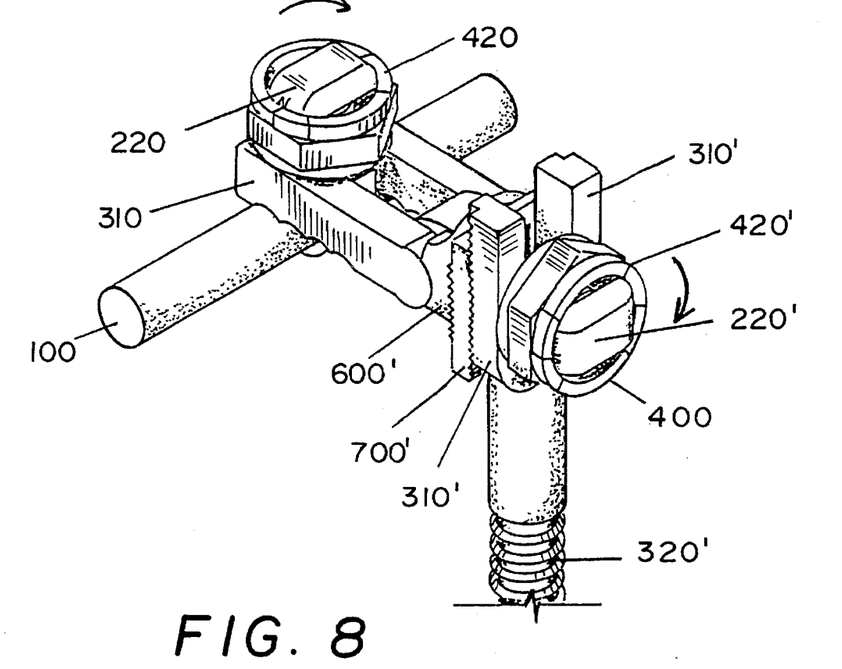
FIG. 8 shows a perspective view of another two sets of embodiments in combination according to the present invention.

The reference numerals of FIGS. 7 and 8 are similar in definition to the like reference numerals of FIG. 1. The component parts of FIGS. 7 and 8 are similar in construction to the like component parts of FIG. 1. The U-shaped connection element 300 is of a combination type and is made up of fitting arms 301, 303, tubular bodies 302, 304, and the connecting portion 320, in which the tubular body 302(101') having male threads engageable with female threads provided in the inner wall of the tubular body 304(102'). The tubular bodies 302 and 304 are engaged with each other to form a rod body 100' for another set of the retaining mechanism of the vertebral fixation rod, and the connecting portion 320 here also serves as a retaining bolt 200' of this another set of the retaining mechanism of the vertebral fixation rod, which is made up of a retaining ring 210' and a bolt portion containing a rectangular head 220' which is provided with a retaining slot 221'.

What is claimed is:

1. A retaining mechanism of a vertebral fixation rod comprising:

a retaining bolt provided at one end thereof with a retaining ring for holding a rod body, said retaining bolt further provided at another end thereof with a bolt portion having a rectangular head;

a U-shaped connection element provided at one end thereof with a U-shaped fitting portion dimensioned to fit over said bolt portion of said retaining bolt, said U-shaped connection element further provided at another end thereof with a connecting portion engageable with a vertebra to be fixed or with a vertebral fixation device; and a fastening nut engageable with said rectangular head of said bolt portion of said retaining bolt, said fastening nut provided therein with a plurality of bevel slide blocks for enabling said retaining bolt to slide along said bevel slide blocks when said fastening nut is rotated, and said fastening nut further provided with at least one stop element adapted to stop said fastening nut when it is rotated to a predetermined degree by engaging the at least one stop element with the rectangular head of the retaining bolt.

2. The retaining mechanism of a vertebral fixation rod as defined in claim 1 further comprising, in combination a rod body, wherein said rod body is a fixation rod.

3. The retaining mechanism of a vertebral fixation rod as defined in claim 1 further comprising, in combination a rod body, wherein said rod body is a connection rod body.

4. The retaining mechanism of a vertebral fixation rod as defined in claim 1, wherein said fastening nut has an inner diameter greater than the length of a long side of said rectangular head of said retaining bolt; and wherein said fastening nut further has a rectangular space having a short side distance intermediary between the length of said long side of said rectangular head and the length of said short side of said rectangular head.

5. The retaining mechanism of a vertebral fixation rod as defined in claim 4 further comprising an angle adjusting washer adapted to fit about the bolt portion of said retaining bolt.

6. The retaining mechanism of a vertebral fixation rod as defined in claim 4, further comprising a height adjusting washer adapted to fit about the bolt portion of said retaining bolt.

7. The retaining mechanism of a vertebral fixation rod as defined in claim 4, further comprising a distance adjusting connection element adapted to fit about the bolt portion of said retaining bolt.

8. The retaining mechanism of a vertebral fixation rod as defined in claim 4, further comprising an offset connector adapted to fit about the bolt portion of said retaining bolt.

9. The retaining mechanism of a vertebral fixation rod as defined in claim 1 further comprising an angle adjusting washer adapted to fit about the bolt portion of said retaining bolt.

10. The retaining mechanism of a vertebral fixation rod as defined in claim 1, wherein said plurality of bevel slide blocks of the fastening nut comprise two bevel slide blocks arranged on two opposite sides of an inner surface of the fastening nut such that an interior of the fastening nut is provided with a rectangular space dimensioned to allow the rectangular head of the retaining bolt to pass therethrough.

11. The retaining mechanism of a vertebral fixation rod as defined in claim 10, wherein the two bevel slide blocks has a bevel slide surface and a platform, and a line connecting two edges between the platforms and the bevel slide surfaces intersects a central axis of the fastening nut.

12. The retaining mechanism of a vertebral fixation rod as defined in claim 1, further comprising a height adjusting washer adapted to fit about the bolt portion of said retaining bolt.

13. The retaining mechanism of a vertebral fixation rod as defined in claim 1, further comprising a distance adjusting connection element adapted to fit about the bolt portion of said retaining bolt.

14. The retaining mechanism of a vertebral fixation rod as defined in claim 1, further comprising an offset connector adapted to fit about the bolt portion of said retaining bolt.

15. The retaining mechanism of a vertebral fixation rod as defined in claim 1, wherein said fastening nut is of a circular construction.

* * * * *